United States Patent
Audousset

(10) Patent No.: US 7,135,046 B2
(45) Date of Patent: Nov. 14, 2006

(54) DYE COMPOSITION COMPRISING AT LEAST ONE OXIDATION BASE CHOSEN FROM 4,5-DIAMINO-1-(β-HYDROXYETHYL)-1H-PYRAZOLE AND 4,5-DIAMINO-1-(β-METHOXYETHYL)-1H-PYRAZOLE AND THE ADDITION SALTS THEREOF AND AT LEAST ONE COUPLER CHOSEN FROM 6-HYDROXYINDOLE AND THE ADDITION SALTS THEREOF

(75) Inventor: Marie-Pascale Audousset, Asnieres (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 10/871,005

(22) Filed: Jun. 21, 2004

(65) Prior Publication Data

US 2005/0015897 A1    Jan. 27, 2005

Related U.S. Application Data

(60) Provisional application No. 60/506,721, filed on Sep. 30, 2003.

(30) Foreign Application Priority Data

Jun. 19, 2003    (FR) ................................ 03 07401

(51) Int. Cl.
*A61K 7/13* (2006.01)
(52) U.S. Cl. ................ 8/405; 8/406; 8/409; 8/410; 8/421; 8/570; 548/300
(58) Field of Classification Search .................. 8/405, 8/406, 409, 410, 421, 570; 548/300
See application file for complete search history.

(56) References Cited

U.S. PATENT DOCUMENTS

| RE30,199 E | 1/1980 | Rose et al. .................. 8/10.2 |
| 4,823,985 A | 4/1989 | Grollier et al. ............. 222/105 |
| 5,061,289 A | 10/1991 | Clausen et al. ................ 8/405 |
| 5,380,340 A | 1/1995 | Neunhoeffer et al. |
| 5,534,267 A | 7/1996 | Neunhoeffer et al. ........ 424/701 |
| 5,663,366 A | 9/1997 | Neunhoeffer et al. .... 548/371.4 |
| 5,766,576 A | 6/1998 | Lowe et al. .................. 424/62 |
| 6,099,592 A | 8/2000 | Vidal et al. .................... 8/409 |
| 6,284,003 B1 | 9/2001 | Rose et al. .................... 8/412 |
| 6,730,789 B1 | 5/2004 | Birault et al. ................ 546/121 |
| 2003/0000027 A1 | 1/2003 | Hoeffkes et al. ................ 8/405 |
| 2003/0131423 A1* | 7/2003 | Javet et al. .................... 8/405 |
| 2004/0216242 A1 | 11/2004 | Kravtchenko et al. .......... 8/405 |

FOREIGN PATENT DOCUMENTS

| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| DE | 199 62 871 A1 | 6/2001 |
| DE | 199 62 872 A1 | 6/2001 |
| DE | 100 37 158 | 2/2002 |
| DE | 201 18 089 | 2/2002 |
| EP | 0 375 977 B1 | 7/1990 |
| EP | 0 770 375 B1 | 5/1997 |
| FR | 2 586 913 | 9/1985 |
| FR | 2 733 749 | 11/1996 |
| FR | 2 801 308 | 5/2001 |
| GB | 1026978 | 4/1966 |
| GB | 1153196 | 5/1969 |
| JP | 63-169571 | 1/1990 |
| WO | WO 94/08969 | 4/1994 |
| WO | WO 94/08970 | 4/1994 |
| WO | WO 96/15765 | 5/1996 |
| WO | WO 02/46165 | 6/2002 |
| WO | WO 02/072556 | 9/2002 |
| WO | WO 03/028688 A1 | 4/2003 |

OTHER PUBLICATIONS

English language Derwent Abstract of DE 100 37 158, Feb. 7, 2002.
English language Derwent Abstract of DE 201 18 089, Feb. 21, 2002.
English Abstract to DE 199 62 872.
English Abstract to EP 0 770 375.
English Abstract to JP 63-169571 (JP 02-01956).

* cited by examiner

*Primary Examiner*—Eisa Elhilo
(74) *Attorney, Agent, or Firm*—Finnegan, Henderson, Farabow, Garrett & Dunner, LLP

(57) ABSTRACT

The invention relates to a composition for the oxidation dyeing of keratin fibers, for example, human keratin fibers such as the hair, comprising at least one oxidation base chosen from 4,5-diamino-1-(β-hydroxyethyl)-1H-pyrazole and 4,5-diamino-1-(β-methoxyethyl)-1H-pyrazole, and the addition salts therof and at least one coupler chosen from 6-hydroxyindole and the addition salts therof. The invention also relates to a dyeing process using this composition.

19 Claims, No Drawings

DYE COMPOSITION COMPRISING AT LEAST ONE OXIDATION BASE CHOSEN FROM 4,5-DIAMINO-1-(β-HYDROXYETHYL)-1H-PYRAZOLE AND 4,5-DIAMINO-1-(β-METHOXYETHYL)-1H-PYRAZOLE AND THE ADDITION SALTS THEREOF AND AT LEAST ONE COUPLER CHOSEN FROM 6-HYDROXYINDOLE AND THE ADDITION SALTS THEREOF

This application claims benefit of U.S. Provisional Application No. 60/506,721, filed Sep. 30, 2003.

The disclosure relates to a composition, for example, for the oxidation dyeing of keratin fibres, for example, human keratin fibres such as the hair, comprising at least one oxidation base chosen from 4,5-diamino-1-(β-hydroxyethyl)-1H-pyrazole and 4,5-diamino-1-(β-methoxyethyl)-1H-pyrazole; and 6-hydroxyindole as a coupler.

It is known practice to dye keratin fibres, for example, human keratin fibres such as hair, with dye compositions comprising oxidation dye precursors, which are generally known as oxidation bases, such as ortho- or para-phenylenediamines, ortho- or para-aminophenols and heterocyclic compounds. These oxidation bases are colourless or weakly coloured compounds which, when combined with oxidizing products, can give rise to coloured compounds by a process of oxidative condensation.

It is also known that the shades obtained with these oxidation bases can be varied by combining them with couplers or coloration modifiers, these agents being chosen from, for example, aromatic meta-diamines, meta-aminophenols, meta-diphenols and certain heterocyclic compounds such as indole compounds.

The variety of molecules used as oxidation bases and couplers allows a wide range of colours to be obtained.

The "permanent" coloration obtained by means of these oxidation dyes may moreover satisfy a certain number of requirements. Thus, it may have no toxicological drawback, it may allow shades to be obtained in the desired strength, and it may show good fastness with respect to external agents such as light, bad weather, washing, permanent-waving, perspiration and rubbing.

The dyes may also allow white hair to be covered and, finally, they may be as unselective as possible, i.e. they must produce the smallest possible differences in coloration along the same keratin fibre, which is generally differently sensitized between its end and its root.

Compositions for the oxidation dyeing of keratin fibres, comprising a 3,4- or 4,5-diaminopyrazole as oxidation base, in combination with couplers conventionally used for the oxidation dyeing of keratin fibres, have already been proposed, such as in patent application EP 0 375 977.

German patent applications DE 199 62 871 and DE 199 62 872 describe compositions for the oxidation dyeing of keratin fibres, comprising a 4,5-diaminopyrazole derivative as an oxidation base, in combination with a suitably selected meta-aminophenol derivative as coupler.

German patent application DE 100 37 158 describes compositions for the oxidation dyeing of keratin fibres, comprising a suitably selected 4,5-diaminopyrazole derivative and a suitably selected para-phenylenediamine derivative as oxidation bases, in combination with couplers conventionally used in the oxidation dyeing of keratin fibres.

German patent application DE 201 18 089 describes compositions for the oxidation dyeing of keratin fibres, comprising a 4,5-diaminopyrazole derivative of given general formula as oxidation base, in combination with couplers conventionally used in the oxidation dyeing of keratin fibres.

Patent application WO 02/46165 describes compositions for the oxidation dyeing of keratin fibres, comprising a 4,5-diaminopyrazole derivative of given general formula as an oxidation base.

Patent application WO 03/028688 describes compositions for the oxidation dyeing of keratin fibres, comprising a 4,5-diaminopyrazole derivative of given general formula as an oxidation base, in combination with heterocyclic oxidation bases other than 4,5-diaminopyrazole derivatives, and couplers conventionally used in the oxidation dyeing of keratin fibres.

However, the compositions described in the prior art may not be entirely satisfactory, especially with regard to the variety of shades that may be obtained, and also with regard to the fastness of the colorations obtained with respect to the various attacking factors to which the hair may be subjected, and in particular with respect to shampoo and permanent-reshaping operations, and with regard to the strength of the colorations obtained.

The aim of the present disclosure is to provide novel compositions for the oxidation dyeing of keratin fibres. For example, in one embodiment, the aim of the present disclosure is to provide novel compositions that produce original, strong, aesthetic, sparingly selective colorations that show good resistance to the various attacking factors to which the hair may be subjected, such as shampoo, light, sweat and permanent-reshaping operations.

One non-limiting embodiment is a composition for the oxidation dyeing of keratin fibres, comprising, in a suitable dyeing medium:

at least one oxidation base chosen from 4,5-diamino-1-(β-hydroxyethyl)-1H-pyrazole and 4,5-diamino-1-(β-methoxyethyl)-1H-pyrazole, and the addition salts thereof; and at least one coupler chosen from 6-hydroxyindole, and the addition salts thereof.

The composition of the present invention may, for example, produce at least one of a chromatic, strong, aesthetic, sparingly selective and fast coloration of keratin fibres in more natural shades, such as mahogany colours.

A subject of the disclosure is also a process for the oxidation dyeing of keratin fibres, for example, of human keratin fibres such as the hair, using this composition.

In one embodiment, the composition disclosed herein comprises at least one oxidation base chosen from 4,5-diamino-1-(β-hydroxyethyl)-1H-pyrazole and the addition salts thereof.

The composition of the present invention may further comprise at least one additional oxidation base chosen from the oxidation bases conventionally used in oxidation dyeing other than 4,5-diamino-1-(β-hydroxyethyl)-1H-pyrazole and 4,5-diamino-1-(β-methoxyethyl)-1H-pyrazole. By way of example, the at least one additional oxidation base is chosen from para-phenylenediamines, bis(phenyl)alkylenediamines, para-aminophenols, ortho-aminophenols and heterocyclic bases other than 4,5-diamino-1-(β-hydroxyethyl)-1H-pyrazole and 4,5-diamino-1-(β-methoxyethyl)-1H-pyrazole, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-ethyl-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-thienyl-para-phenylenediamine and 2-(β-hydroxyethylamino)-5-aminotoluene, and the addition salts thereof.

Among the para-phenylenediamines, non-limiting mention may be made of para-phenylenediamine, para-tolylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 2-chloro-para-phenylenediamine and 2-(β-acetylaminoethyloxy)-para-phenylenediamine, and the addition salts thereof.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2-chlorophenol, 4-amino-2,6-dichlorophenol, 4-amino-6-((5'-amino-2'-hydroxy-3'-methylphenyl)methyl)-2-methylphenol and bis(5-amino-2-hydroxyphenyl)methane, and the addition salts thereof.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives other than 4,5-diamino-1-(β-hydroxyethyl)-1H-pyrazole and 4,5-diamino-1-(β-methoxyethyl)-1H-pyrazole.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-yl-pyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]-pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives other than 4,5-diamino-1-(β-hydroxyethyl)-1H-pyrazole and 4,5-diamino-1-(β-methoxyethyl)-1H-pyrazole that may be mentioned are, for example, the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl4,5-diamino-3-methylpyrazole, 4,5-diamino-3-tert-butyl-1-methylpyrazole, 4,5-diamino-1-tert-butyl-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methyl-pyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triamino-pyrazole, 3,5-diamino-1-methyl-4-methylaminopyrazole and 3,5-diamino4-(β-hydroxyethyl)-amino-1-methyl-pyrazole, and the addition salts thereof.

In the presence of additional oxidation bases, these bases are chosen from, for example, bis(phenyl)alkylenediamines, para-aminophenols, ortho-aminophenols and heterocyclic bases other than 4,5-diamino-1-(β-hydroxyethyl)-1H-pyrazole and 4,5-diamino-1-(β-methoxyethyl)-1H-pyrazole, and the addition salts thereof.

In some embodiments the composition disclosed herein comprises as the only oxidation bases at least one oxidation base chosen from 4,5-diamino-1-(β-hydroxyethyl)-1H-pyrazole and 4,5-diamino-1-(β-methoxyethyl)-1H-pyrazole, and the addition salts thereof.

The at least one oxidation base present in the composition of the invention is generally present in an amount ranging from 0.001% to 10% by weight, such as from 0.005% to 6%, relative to the total weight of the dye composition.

In addition to 6-hydroxyindole, the composition disclosed herein may comprise at least one additional coupler chosen from the couplers conventionally used for the oxidation dyeing of keratin fibres. Among these couplers, non-limiting mention may be made of meta-phenylenediamines, meta-aminophenols, meta-diphenols, naphthalene-based couplers and heterocyclic couplers other than 6-hydroxyindole, and also the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureido-aniline, 3-ureido-1-dimethylaminobenzene, sesamol, 1-β-hydroxyethylamino-3,4-methylenedioxybenzene, α-naphthol, 2-methyl-1-naphthol, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

According to one embodiment of the invention, the composition comprises as sole coupler at least one coupler chosen from 6-hydroxyindole and the addition salts thereof.

In the composition disclosed herein, the at least one coupler is generally present in an amount ranging from approximately 0.001% to 10% by weight, such as from 0.005% to 6%, relative to the total weight of the dye composition.

In general, the addition salts of the at least one oxidation base and of the at least one couplerthat may be used in the context of the disclosure are chosen, for example, from the addition salts with an acid, such as the hydrochlorides, hydrobromides, sulphates, citrates, succinates, tartrates, lactates, tosylates, benzenesulphonates, phosphates and acetates; and the addition salts with a base, such as sodium hydroxide, potassium hydroxide, aqueous ammonia, amines or alkanolamines.

In some embodiments, the dye composition disclosed herein may further comprise at least one direct dye that may be chosen from, for example, nitrobenzene dyes, azo direct dyes, and methine direct dyes. These direct dyes may, for example, be of nonionic, anionic or cationic nature.

The medium that is suitable for dyeing, also known as a dye support, generally comprises water or of a mixture of water and of at least one organic solvent to dissolve the compounds that would not be sufficiently soluble in the water. Examples of organic solvents that may be mentioned include, for example, $C_1$–$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether; and aromatic alcohols, for instance benzyl alcohol or phenoxyethanol, and mixtures thereof.

The solvents are present in amounts ranging from 1% to 40% by weight, such as from 5% to 30% by weight relative to the total weight of the dye composition.

The dye composition disclosed herein may further comprise various adjuvants conventionally used in hair dye compositions, such as anionic, cationic, nonionic, amphoteric or zwitterionic surfactants or mixtures thereof; anionic, cationic, nonionic, amphoteric or zwitterionic polymers or mixtures thereof; mineral or organic thickeners, for example, anionic, cationic, nonionic and amphoteric polymeric associative thickeners; antioxidants; penetrating agents; sequestering agents, fragrances, buffers, dispersants, conditioners, for instance volatile or non-volatile, modified or unmodified silicones, film-forming agents, ceramides, preserving agents and opacifiers.

The above adjuvants are each generally present in an amount ranging from 0.01% to 20% by weight relative to the total weight of the composition.

Needless to say, a person skilled in the art will take care to select this or these additional optional compound(s) such that the advantageous properties intrinsically associated with the oxidation dye composition in accordance with the disclosure are not, or are not substantially, adversely affected by the envisaged addition(s).

The pH of the dye composition disclosed herein generally ranges from 3 to 12, for example, from 7 to 12 such as, for example, from 7.5 to 1 1. The pH of the dye composition may be adjusted to the desired value by using acidifying or basifying agents usually used for dyeing keratin fibres, or alternatively using standard buffer systems.

Among the acidifying agents that may be mentioned, for example, are mineral or organic acids, for instance hydrochloric acid, orthophosphoric acid, sulphuric acid, carboxylic acids, for instance acetic acid, tartaric acid, citric acid or lactic acid, and sulphonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (I) below:

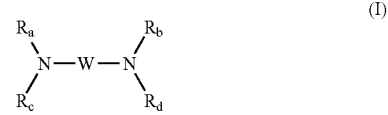

(I)

wherein W is a propylene residue optionally substituted with a substituent chosen from hydroxyl groups and $C_1$–$C_4$ alkyl radicals; $R_a$, $R_b$, $R_c$ and $R_d$, which may be identical or different, are chosen from hydrogen atoms, $C_1$–$C_4$ alkyl radicals, and $C_1$–$C_4$ hydroxyalkyl radicals.

The dye composition disclosed herein may be in various forms, such as in the form of liquids, creams or gels, or in any other form that is suitable for dyeing keratin fibres, such as human hair.

The process of the present disclosure is, for example, a process in which the composition disclosed herein is applied to the keratin fibres, and the colour of the keratin fibres is developed using an oxidizing agent. The colour may be developed at an acidic, neutral or alkaline pH. The colour may be developed, for example, at a pH ranging from 7 to 12. The oxidizing agent may be added to the composition disclosed herein just at the time of use, or it may be employed using an oxidizing composition comprising it, applied simultaneously with or sequentially to the composition of the invention.

According to one embodiment, the composition disclosed herein is mixed, for example, at the time of use, with a composition comprising, in a medium that is suitable for dyeing, at least one oxidizing agent, this oxidizing agent being present in an amount that is sufficient to develop a coloration. The mixture obtained is then applied to the keratin fibres. After a leave-in time of 3 to 50 minutes and, for example, from5 to 30 minutes, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulphates, peracids, and oxidase enzymes, among which mention may be made of peroxidases, 2-electron oxidoreductases such as uricases, and 4-electron oxygenases, for instance laccases. Hydrogen peroxide, for example, may be used.

The oxidizing composition may further comprise various adjuvants conventionally used in hair dye compositions and as defined above.

The pH of the oxidizing composition containing the oxidizing agent is such that, after mixing with the dye composition, the pH of the resulting composition applied to the keratin fibres ranges from 3 to 12, for example, from 7 to 12, such as from 7.5 to 11. The pH may be adjusted to the desired value by using acidifying or basifying agents usually used in the dyeing of keratin fibres and as defined above.

The ready-to-use composition that is finally applied to the keratin fibres may be in various forms, such as in the form of liquids, creams or gels, or in any other form that is suitable for dyeing keratin fibres, such as human hair.

A subject of the disclosure is also a multi-compartment device, or dyeing "kit", comprising a first compartment which comprises the dye composition disclosed herein and a second compartment which comprises an oxidizing agent. This device may be equipped with a means for applying the desired mixture to the hair, such as the devices described in patent FR 2 586 913 in the name of the Applicant.

Using this device, it is possible to dye keratin fibres using a process that involves mixing the dye composition disclosed herein with an oxidizing agent as defined above, and applying the mixture obtained to the keratin fibres for a time that is sufficient to develop the desired coloration.

The examples that follow serve to illustrate the invention without, however, being limiting in nature.

EXAMPLES

A dye composition was prepared as indicated below:

| Example | 1 |
|---|---|
| 4,5-Diamino-1-(β-hydroxyethyl)-1H-pyrazole dihydrochloride | 1.075 g |
| 6-Hydroxyindole | 0.665 g |
| Dye support | (*) |
| Demineralized water qs | 100 g |

(*): common dye support
| | |
|---|---|
| Oleyl alcohol polyglycerolated with 2 mol of glycerol | 4 g |
| Oleyl alcohol polyglycerolated with 4 mol of glycerol (78% A.M.) | 5.69 g A.M. |
| Oleic acid | 3.0 g |
| Oleylamine containing 2 mol of ethylene oxide, sold under the trade name Ethomeen O12 by the company Akzo | 7 g |
| Diethylaminopropyl laurylaminosuccinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution containing 35% A.M. | 0.455 g A.M. |
| Ammonium acetate | 0.8 g |
| Antioxidant, sequestering agent | qs |
| Fragrance, preserving agent | qs |
| Aqueous ammonia containing 20% NH$_3$ | 10.0 g |

The composition was mixed extemporaneously with its equivalent weight of 20-volumes aqueous hydrogen peroxide solution, the pH of which is 3.

The pH of the composition obtained after mixing was about 9.8.

The mixture thus prepared was applied to locks of permanent-waved grey hair comprising 90% white hairs, at a rate of 30 g per 3 g of hair, for 30 minutes. The hair was then rinsed, washed with a standard shampoo and dried.

The hair coloration was evaluated visually. The shades obtained are given in the table below.

| Tone height | Glint |
|---|---|
| Dark blond | Mahogany |

What is claimed is:

1. A composition for the oxidation dyeing of keratin fibres, comprising, in a suitable dyeing medium:
    at least one oxidation base chosen from 4,5-diamino-1-(β-hydroxyethyl)-1H-pyrazole and the addition salts thereof; and
    at least one coupler chosen from 6-hydroxyindole, and the addition salts thereof.

2. The composition according to claim 1, comprising at least one additional oxidation base chosen from para-phenylenediamines, bis(phenyl)-alkylenediamines, para-aminophenols, ortho-aminophenols, heterocyclic bases and the addition salts thereof other than 4,5-diamino-1-(β-hydroxyethyl)-1H-pyrazole and 4,5-diamino-1-(β-methoxyethyl)-1H-pyrazole, and the addition salts thereof.

3. The composition according to claim 2, wherein the at least one additional oxidation base is chosen from bis(phenyl)alkylenediamines, para-aminophenols, ortho-aminophenols, heterocyclic bases and the addition salts thereof other than 4,5-diamino-1-(β-hydroxyethyl)-1H-pyrazole and 4,5-diamino-1-(β-methoxyethyl)-1H-pyrazole, and the addition salts thereof.

4. The composition according to claim 1, comprising as the only oxidation bases at least one oxidation base chosen from 4,5-diamino-1-(β-hydroxyethyl)-1H-pyrazole and the addition salts thereof.

5. The composition according to claim 1, further comprising at least one additional coupler chosen from meta-phenylenediamines, meta-aminophenols, meta-diphenols, naphthalene-based couplers, heterocyclic couplers other than 6-hydroxyindole, and the addition salts thereof.

6. The composition according to claim 1, wherein the amount of each of the at least one oxidation base ranges from 0.001% to 10% by weight relative to the total weight of the dye composition.

7. The composition according to claim 1, wherein the at least one coupler ranges from 0.001% to 10% by weight relative to the total weight of the dye composition.

8. The composition according to claim 1, having a pH ranging from 3 to 12.

9. The composition according to claim 8, having a pH ranging from 7 to 12.

10. The composition according to claim 1, wherein the composition further comprises at least one oxidizing agent.

11. The composition according to claim 10, wherein the at least one oxidizing agent is chosen from hydrogen peroxide, urea peroxide, alkali metal bromates, persalts, peracids and oxidase enzymes.

12. The composition according to claim 10, having a pH ranging from 7 to 12.

13. A process for the oxidation dyeing of keratin fibres, comprising applying to the keratin fibres a composition comprising, in a suitable dyeing medium
at least one oxidation base chosen from 4,5-diamino-1-(β-hydroxyethyl)-1H-pyrazole and the addition salts thereof; and at least one coupler chosen from 6-hydroxyindole, and the addition salts thereof; and at least one oxidizing agent for developing the colour of the keratin fibres.

14. The process according to claim 13, wherein the composition has a pH ranging from 7 to 12.

15. The process according to claim 13, wherein the at least one oxidizing agent is chosen from hydrogen peroxide, urea peroxide, alkali metal bromates, persalts, peracids and oxidase enzymes.

16. The process according to claim 13, wherein the at least one oxidizing agent is mixed at the time of use with the composition.

17. The process according to any one of claim 13, wherein the oxidizing agent is applied to the keratin fibres in the form of an oxidizing composition, simultaneously with or sequentially to the composition.

18. A multi-compartment device, comprising
a first compartment comprising a dye composition comprising in a suitable dyeing medium:
at least one oxidation base chosen from 4,5-diamino-1-(β-hydroxyethyl)-1H-pyrazole and the addition salts thereof; and
at least one coupler chosen from 6-hydroxyindole, and the addition salts thereof; and
a second compartment comprising at least one oxidizing agent.

19. The multi-compartment device of claim 18, wherein the at least one oxidizing agent is chosen from hydrogen peroxide, urea peroxide, alkali metal bromates, persalts, peracids and oxidase enzymes.

* * * * *

UNITED STATES PATENT AND TRADEMARK OFFICE
CERTIFICATE OF CORRECTION

| | | |
|---|---|---|
| PATENT NO. | : 7,135,046 B2 | Page 1 of 1 |
| APPLICATION NO. | : 10/871005 | |
| DATED | : November 14, 2006 | |
| INVENTOR(S) | : Marie-Pascale Audousset | |

It is certified that error appears in the above-identified patent and that said Letters Patent is hereby corrected as shown below:

On the title page, item (57), line 6, "therof" should read --thereof--.

On the title page, item (57), line 7, "therof" should read --thereof--.

Column 8, line 29, "bis(phenyl)-alkylenediamines," should read --bis(phenyl)alkylenediamines--.

Column 10, line 1, "to any one of claim" should read --to claim--.

Signed and Sealed this

Fourth Day of September, 2007

JON W. DUDAS
*Director of the United States Patent and Trademark Office*